United States Patent [19]

Ahmad et al.

[11] Patent Number: 4,999,342

[45] Date of Patent: Mar. 12, 1991

[54] LONG LASTING CONTRACEPTIVE SUPPOSITORY COMPOSITION AND METHODS OF USE

[75] Inventors: Nawaz Ahmad, Piscataway; George A. Ziets, Flemington; Sudeb Das, Dayton Square, all of N.J.

[73] Assignee: Ortho Pharmaceutical Corporation, Raritan, N.J.

[21] Appl. No.: 232,816

[22] Filed: Aug. 16, 1988

[51] Int. Cl.$^5$ .............................................. A61K 31/00
[52] U.S. Cl. ...................................... 514/54; 514/23; 514/57; 514/63; 514/841; 514/843; 514/967; 424/DIG. 14; 424/DIG. 15
[58] Field of Search ...................... 514/54, 23, 57, 63, 514/841, 843, 967; 424/DIG. 14, DIG. 15

[56] References Cited

U.S. PATENT DOCUMENTS

| | | | |
|---|---|---|---|
| 4,187,286 | 2/1980 | Marcus | 514/263 |
| 4,551,148 | 11/1985 | Riley, Jr. et al. | 424/DIG. 14 |
| 4,659,696 | 4/1987 | Hirai et al. | 514/16 |

*Primary Examiner*—Ronald W. Griffin
*Assistant Examiner*—Everett White

[57] ABSTRACT

Compositions and methods for providing long lasting contraceptive protection comprising a mixture of a contraceptive effective amount of spermicidal agent, a polymeric gum, a dispersing agent, and a water miscible polyethylene glycol polymer suppository base; and mammalian contraceptive methods utilizing the compositions of the invention in suppository form to provide up to 12 hours of contraceptive protection after initial insertion of the suppository.

15 Claims, No Drawings

4,999,342

LONG LASTING CONTRACEPTIVE SUPPOSITORY COMPOSITION AND METHODS OF USE

FIELD OF THE INVENTION

This invention relates to a long lasting contraceptive suppository composition. More particularly, this invention relates to a contraceptive suppository composition comprising a spermicide and a viscous adhesive composition which provides long lasting contraceptive action.

BACKGROUND OF THE INVENTION

Conventional vaginal contraceptive products utilizing a spermicidal agent provide a very limited duration of contraception. Conventional methods of spermicidal contraception require that the products need to be inserted into the vagina not more than one hour preferably 10–30 minutes before coitus for suppository products and even less time for foam and gel products. In view of such time constraints these products must be reapplied if coitus is repeated more than one hour after the original insertion. While various attempts have been made in the art to provide a longer lasting and more convenient vaginal contraceptive spermicidal suppository, they have met with only limited success.

Riley, Jr. et al. in U.S. Pat. No. 4,551,148 describe a vaginal delivery system which is allegedly bio-adherent to the vaginal surface and releases an active agent in a controlled manner for at least three hours to a receptor site. Foamable-type vaginal suppository compositions have also been developed, but such have not been found to provide effective contraceptive activity for long periods of time.

It is therefore an object of the present invention to provide a novel vaginal contraceptive suppository which has a long period of contraceptive activity and is highly effective in preventing conception due to coitus for up to 12 hours after initial insertion of the suppository.

SUMMARY OF THE INVENTION

The foregoing object of providing a long lasting vaginal contraceptive suppository has now been accomplished in accordance with the compositions and methods of the present invention.

In accordance with the purposes of the invention, as embodied and fully described herein, the invention comprises a long lasting contraceptive suppository composition comprising a mixture of a contraceptive effective amount of spermicidal agent; a polymeric gum; a dispersing agent; and a water-miscible polyethylene glycol polymer suppository base. The polymeric gum provides viscous adhesive qualities to the mixture. The dispersing agent contributes homogeneous melt and spread characteristics to the mixture and acts to absorb and hold the spermicidal agent to provide a controlled release of the agent over several hours.

In preferred embodiments of the composition of the invention the polymeric gum is a polysaccaharide gum, particularly carboxymethylcellulose, xanthan gum and mixtures thereof; the dispersing agent is fumed silica, silica gel or mixtures thereof; and the spermicidal agent is preferably water-soluble. and particular examples include nonoxynol-9, octoxynol-9, menfegol, benzalkonium chloride or mixtures thereof. Preferred proportions of ingredients are, by weight of the total suppository composition, from 10–30% by weight of spermicidal agent; from 15 to 25% by weight of polymeric gum; from about 1 to 5% but more preferably about 1.5 to 4.0% by weight of the dispersing agent; and from 41% to 73.5% of the suppository base material comprising water miscible polyethylene glycol polymer.

The invention also comprises a method for providing long-lasting contraceptive protection to mammals which comprises the steps of: inserting into the vicinity of the cervix in the vagina of a warm blood mammal a composition comprising a contraceptive effective amount of spermicidal agent, a sufficient amount of polymeric gum to induce viscous qualities to the spermicidal agent, a sufficient amount of dispersing agent to provide homogeneous melt characteristics to the suppository composition, and a water miscible polyethylene glycol polymer; and engaging in an act of coitus up to 5 to 12 hours after insertion of the suppository composition.

DETAILED DESCRIPTION OF THE PREFERRED EMBODIMENTS OF THE INVENTION

Reference will now be made in detail to preferred embodiments of the invention, examples of which are illustrated in the following examples section.

The long lasting contraceptive suppository composition of the invention provides reliable protection against conception for a prolonged period of time after insertion of the suppository into the vagina. While conventional vaginal suppositories provide spermicidal protection against conception for up to 1 hour, reapplication is necessary if coitus is repeated. The composition of the present invention can be used in a single application to insure contraception for up to 12 hours because the spermicidal agent is adhered and retained for up to 12 hours throughout the vagina and cervix.

The unique formulation of the composition of the invention provides a quick melting suppository base whereby a viscous solution of spermicide adheres to the body of the vagina and entrance to the cervix as the suppository melts thus setting up a protective barrier of spermicide. The protective barrier of spermicidal agent will rapidly kill all sperm on contact or immobilize the sperm and render them unable to fertilize.

Spermicidal agents used in the composition of the invention can be any effective spermicidal agent. Water-soluble spermicide agents are preferred because of their compatibility with other preferred components of the suppository composition described herein. Examples of preferred spermicides include nonoxynol-9, octoxynol-9, menfegol, benzalkonium chloride or mixtures thereof.

A dispersing agent, such as fumed silica (colloidal silicon dioxide), silica gel or mixtures thereof, has been found to advantageously provide an even, homogeneous spreading of the spermicidal adhering composition throughout the targeted area of the vagina and the cervix to provide an effective spermicidal barrier against conception. The dispersing agent and particularly fumed silica and silica gels are necessary to provide controlled release of the water soluble spermicidal agent over several hours at the targeted area because of the absorbency and retaining characteristics the dispersing agent imparts to the composition. Further, physical observations reveal that without dispersing agents such as fumed silica or silica gel a homogeneous dispersal of ingredients is not obtained.

The suppository base of the composition of the invention is preferably a water miscible polyethylene glycol polymer (PEG) having a molecular weight range of 200–6000. PEG is preferred because it is compatible with spermicidal agents and will not interfere with the efficacy of such agents. Polyethylene glycol is particularly preferred because of its water solubility whereas more oily, less water-soluble bases are generally not preferred.

The polymeric gums usable in accordance with the invention provide adherence of the spermicide in the vaginal area for up to 12 hours and will eventually dissolve and dissipate from the area. Polysaccaharide gums are preferred because of their safety and acceptability as pharmaceutical excipients for topical application and their effectiveness in accordance with the composition and methods of the invention. Particularly preferred polysaccharide gums usable in accordance with the invention are fine grained carboxymethylcellulose (CMC) and xanthan gum and more preferably, mixtures thereof. Fine-grained CMC is used to provide a smooth, non-grainy product.

In preparing a suppository composition of the invention the following amounts by weight of the total composition are generally used: from about 10–30% by weight spermicidal agent; from about 15–20% by weight of polymeric gum; from about 1 to 5% by weight, preferably, about 1.5 to 4.0% by weight of dispersing agent; and from about 41–74% of suppository base material. The amount of materials used are those that provide a contraceptive effective suppository that is of acceptable size for easy insertion into the vagina. The amounts of material are also selected to provide good melt characteristics to the suppository, i.e. rapid melting and disintegration after insertion into the vagina and exposure to body temperatures therein. Spermicidal agent is included in a proportional amount that provides an effective amount of spermicide against conception. The other components are also used in amounts necessary for carrying out their functions effectively, e.g. a sufficient amount of polymeric gum to provide adherence qualities and enough dispersing agent to homogeneously spread the composition and provide a controlled release of spermicide.

EXAMPLES

The invention will now be illustrated by examples. The examples are not intended to be limiting of the scope of the present invention. In conjunction with the detailed and general description above, the examples provide further understanding of the present invention and an outline of a process for preparing compositions of the invention and practicing the methods of the invention.

The following examples represent preferred embodiments of the compositions, processes and methods of the invention to satisfy the stated objects of the invention. The starting materials and reagents in the examples whose method of preparation are not indicated, are commercially available from sources known to art such as chemical supply houses.

EXAMPLE 1

A long-lasting suppository composition is prepared according to the formulation:

| | |
|---|---|
| Nonoxynol-9 | 20.00% |
| Carboxymethylcellulose | 15.00% |
| Xanthan Gum | 5.00% |
| Silica | 2.50% |
| Suppository Base | q.s. to 100.00% |
| (Polyethylene Glycols 1540/1000:2.88/54.62) | |

The following manufacturing procedure is used. The suppository base, i.e. polyethylene glycols (PEG) with a molecular weight range of 1540/1000 at a ratio of 2.88/54.62 respectively, is melted by heating at about 60° C. The following is added with mixing; spermicide (Nonoxynol-9), fine grain carboxymethylcellulose (CMC), xanthan gum, and silica dispersing agent (i.e. Aerosil 200 brand colloidal silicon dioxide). Mixing is continued for 30 minutes or until the mixture is homogeneous. The mixture is cooled and maintained at a temperature of 40° C.–45° C. and formed into suppositories.

EXAMPLES 2-6

The following examples are prepared in accordance with the manufacturing procedure of Example 1, utilizing the following formulations.

EXAMPLE 2

| | |
|---|---|
| Nonoxynol-9 | 15.00% |
| CMC | 15.00% |
| Xanthan Gum | 5.00% |
| Silica | 2.50% |
| Suppository Base | q.s. to 100.00% |
| (PEG 1450/PEG 1000: 3.12/59.38) | |

EXAMPLE 3

| | |
|---|---|
| Nonoxynol-9 | 10.00% |
| CMC | 15.00% |
| Xanthan Gum | 5.00% |
| Silica | 2.50% |
| Suppository Base | q.s. to 100.00% |
| (PEG 1450/PEG 1000: 3.38/64.12) | |

EXAMPLE 4

| | |
|---|---|
| Menfegol | 20.00% |
| CMC | 15.00% |
| Xanthan Gum | 5.00% |
| Silica | 2.50% |
| Suppository Base | q.s. to 100.00% |
| (PEG 1450/PEG 100: 2.88/54.62) | |

EXAMPLE 5

| | |
|---|---|
| Octoxynol-9 | 30.00% |
| CMC | 20.00% |
| Xanthan Gum | 4.00% |
| Silica | 3.00% |
| Suppository Base | q.s. to 100.00% |
| (PEG 1450/PEG 100: 2.15/40.85) | |

EXAMPLE 6

| | |
|---|---|
| Nonoxynol-9 | 22.50% |
| CMC | 15.00% |
| Xanthan Gum | 5.00% |

| | |
|---|---|
| -continued | |
| Silica | 2.50% |
| Suppository Base<br>(PEG 1540/PEG 100:2.75/52.25) | q.s. to 100.00% |

CONTRACEPTIVE EFFECTIVENESS EVALUATION OF EXAMPLES 1-6

STUMPTAILED MACAQUE MODEL

The stumptailed macaque (*Macaca arctoides*) has previously been established as a good animal model for determining the postcoital spermicidal activity of vaginal preparations*.

*See, Zatuchni et al., Fertility and Sterility, Vol. 35, No. 6 pp. 683–690, 1981.

Long lasting suppository formulations of the invention were delivered to the cervix of female subjects prior to mating. Spermicide activity was determined by a study of semen samples taken from the female subjects immediately following mating at zero hour mating and at twelve hour mating (approximately 10 minutes and 12 hours after insertion of the suppository, respectively). Spermatazoa activity was determined by microscopia observation of sperm movement in the semen sample (i.e. % motility) and of any detectable direction of such movement by the sperm (i.e. % forward progression). The results of the evaluation for various formulations are as follows:

| | % Motility | % Forward Progression |
|---|---|---|
| a Formulation containing 20% Nonoxynol-9 | | |
| Control Mating | 65 | 85 |
| Zero Hour Mating | 0 | 0 |
| Twelve Hour Mating | 0 | 0 |
| b Formulation Containing 15% Nonoxynol-9 | | |
| Control Mating | 65 | 85 |
| Zero Hour Mating | 0 | 0 |
| Twelve Hour Mating | 13 | 43.3 |
| c Formulation Containing 10% Nonoxynol-9 | | |
| Control Mating | 65 | 85 |
| Zero Hour Mating | 0 | 0 |
| Twelve Hour Mating | 0 | 0 |
| d Formulation Containing 20% Menfegol | | |
| Control Mating | 65 | 85 |
| Zero Hour Mating | 0 | 0 |
| Twelve Hour Mating | 0 | 0 |
| e Formulation containing 30% Octoxynol-9 | | |
| Control Mating | 65 | 85 |
| Zero Hour Mating | 0 | 0 |
| Twelve Hour Mating | 79 | 79 |
| f Formulation Containing 2.5% Nonoxynol-9 | | |
| Control Mating | 64 | 84 |
| Zero Hour Mating | 0 | 0 |
| Twelve Hour Mating | 0 | 0 |

IN-VITRO CONTRACEPTIVE EFFECTIVE EVALUATION OF COMPOSITIONS CONTAINING NONOXYNOL-9 USING SANDER-CRAMER METHOD:

The Sander-Cramer Method is a classical method of determining the contraceptive activity of products containing spermicidal agents. This method was used to test the spermicide release over a twelve hour duration from a composition containing Nonoxynol-9. In this study model, 25 ml of normal saline was added to separate sets of 5 jars each, each set containing a separate composition. The jars were tightly closed and incubated at 37° C. At each test interval (0.5,3,6,9 and 12 hours), one jar from each set was removed from the incubator and supernatant from this jar was carefully withdrawn with a pipette and was tested for Nonoxynol-9 concentration. Results were recorded as microgram/ml of Nonoxynol-9 for each sample. It has previously been established that Nonoxynol-9, at a concentration of 125 microgram/ml, completely immobilizes all human spermatozoa. Actual concentration of Nonoxynol-9 was found to be much higher for all test intervals up to twelve (12) hours for all three compositions indicating that Nonoxynol-9 is slowly and continuously released from the composition up to twelve hours and the concentration of Nonoxynol-9 released throughout the twelve hour duration is more than sufficient to be effective for contraception.

a. Formulation Containing 10% Nonoxynol-9:

| Test Interval | Nonoxynol-9 Concentration (micrograms/ml) |
|---|---|
| 30 minutes | 417 |
| 3 hours | 417 |
| 6 hours | 1250 |
| 9 hours | 1250 |
| 12 hours | 2500 | b. Formulation Containing 20% Nonoxynol-9:

| Test Interval | Nonoxynol-9 Concentration (micrograms/ml) |
|---|---|
| 30 minutes | 1250 |
| 3 hours | 1250 |
| 6 hours | 2500 |
| 9 hours | 2500 |
| 12 hours | 2500 | c. Formulation Containing 22.5% Nonoxynol 9:

| Test Interval | Nonoxynol-9 Concentration (Micrograms/ml) |
|---|---|
| 30 minutes | 1250 |
| 3 hours | 2500 |
| 6 hours | 12,500 |
| 9 hours | 2500 |
| 12 hours | 12,500 |

Results

The contraceptive properties of the suppository compositions as described in examples 1-6 were evaluated above. The in vivo data, i.e., the percentage motility and the percentage forward progression of spermatozoa from zero and twelve hour mating indicates that the products are effective contraception after ten minutes to twelve hours from the time of insertion. The Sander-Cramer Method of evaluation also indicated the long acting effectiveness of the composition of the invention.

The scope of the present invention is not limited by the description, examples and suggested uses herein and modifications can be made without departing from the spirit of the invention. For example, other applications of the suppository compositions of the invention are possible, for example, delivering drugs such as antibacterial or antifungal agents into the vagina or other body cavities to provide long lasting exposure of the body area to the active agents.

Application of the compositions and methods of the present invention for contraceptive and other pharmaceutical uses can be accomplished by any suitable therapeutic method and technique as is presently and prospectively known to those skilled in the art. Thus it is intended that the present invention cover the modifications and variations of this invention provided that they come within the scope of the appended claims and their equivalents.

What is claimed is:

1. A long lasting viscous adhesive contraceptive suppository composition comprising a mixture of a contraceptive effective amount of spermicidal agent; a polymeric gum; a dispersing agent comprising silica; and a water miscible polymer suppository base.

2. A composition according to claim 1 wherein the polymeric gum is a polysaccharide gum and the water miscible polymer is polyethylene glycol.

3. A composition according to claim 1 wherein the dispersing agent is fumed silica, colloidal silicon dioxide, silica gel or mixtures thereof.

4. A composition according to claim 1 wherein the spermicidal agent is selected from the group consisting of nonoxynol-9, octoxynol-9, menfegol, benzalkonium chloride, and mixtures thereof.

5. A composition according to claim 4 wherein the polymeric gum is selected from the groups consisting of carboxymethylcellulose, xanthan gum and mixtures thereof; and the dispersing agent is fumed silica or colloidal silicon dioxide.

6. A long lasting contraceptive suppository composition comprising a component mixture of from about 10 to about 30% by weight of spermicidal agent; from about 15 to about 25% by weight of polymeric gum; from about 1 to about 4.0% by weight of dispersing agent comprising silica; and from about 41% to about 74% of suppository base material comprising water miscible polyethylene glycol polymer.

7. A composition according to claim 6 wherein the spermicidal agent is selected from the group consisting of nonoxynol-9, octoxynol-9, menfegol and mixtures thereof; the polymeric gum is selected from the group consisting of carboxymethylcellulose, xanthan gum and mixtures thereof; the dispersing agent is fumed silica or silica gel; and the water miscible polyethylene glycol is a mixture of polymers having molecular weights of from 200 to 6000.

8. A composition according to claim 7 wherein the polymeric gum component is a mixture of from 60 to 85% of carboxymethylcellulose and 15 to 40% of xanthan gum by weight; and the dispersing agent is from 1.5 to 4.0% by weight of fumed silica.

9. A composition according to claim 7 wherein the spermicidal agent is nonoxynol-9.

10. A long lasting mammalian contraceptive method comprising the steps of inserting a suppository composition comprising a component mixture of a contraceptive effective amount of spermicidal agent, a sufficient amount of polymeric gum to induce viscous adhesive qualities to said spermicidal agent, a sufficient amount of dispersing agent to provide homogenous melt characteristics to the suppository composition, and a water miscible polymer suppository base, into the vicinity of the cervix in a vagina of a warm blooded mammal prior to coitus; and engaging therewith in an act of coitus up to over 5 hours after insertion of the suppository compositions.

11. The method according to claim 10 wherein the act of coitus is engaged in a time period of from 10 minutes up to 12 hours after insertion of the suppository composition and the suppository base is polyethylene glycol.

12. The method according to claim 11 wherein the spermicidal agent is selected from the group consisting of nonoxynol-9, octoxynol-9, menfegol, benzalkonium chloride and mixtures thereof; the polymeric gum is selected from the group consisting of carboxymethylcullulose, xanthan gum and mixtures thereof; the dispersing agent is fumed silica or silica gel; and the polyethylene glycol polymer is a mixture of polyethylene glycol having a molecular weight range of between 200 and 6000.

13. The method according to claim 10 wherein the spermicidal agent is nonoxynol-9; the polymeric gum is a mixture of carboxymethylcellulose and xanthan gum; and the dispersing agent is fumed silica.

14. The method according to claim 10 wherein the component mixture is by weight of the total composition from about 10 to 30% of spermicidal agent, from about 15 to 25% of the polymeric gum, from about 1.0 to 5.0% by weight of the dispersing agent, and from about 41% to 74% of polyethylene glycol suppository base material.

15. The method according to claim 14 wherein the spermicidal agent is nonoxynol-9; the polymeric gum component is a mixture of from 60 to 85% of carboxymethylcellulose and from 15 to 40% of xanthan gum; and the dispersing agent is from 1.5 to 4.0% fumed silica.

* * * * *